United States Patent [19]
Esser

[11] Patent Number: 6,106,543
[45] Date of Patent: Aug. 22, 2000

[54] MEDICAL INSTRUMENT DRIVING MEMBER AND END EFFECTOR CONNECTION

[76] Inventor: Theodor Esser, 3 Temple Rd., Setauket, N.Y. 11733

[21] Appl. No.: 09/079,482

[22] Filed: May 15, 1998

[51] Int. Cl.$^7$ .................................................. A61B 17/28
[52] U.S. Cl. ............................................................ 606/205
[58] Field of Search ................................. 606/167, 170, 606/205; 600/567

[56] References Cited

U.S. PATENT DOCUMENTS

| | | | |
|---|---|---|---|
| 5,133,727 | 7/1992 | Bales et al. | 606/170 |
| 5,238,002 | 8/1993 | Devlin et al. | 600/564 |
| 5,241,968 | 9/1993 | Slater | 600/564 |
| 5,582,617 | 12/1996 | Klieman et al. | 606/170 |
| 5,666,965 | 9/1997 | Bales et al. | 128/606 |
| 5,690,673 | 11/1997 | Koscher et al. | 606/205 |
| 5,697,949 | 12/1997 | Ciurtino et al. | 606/205 |
| 5,810,876 | 9/1998 | Kelleher | 606/205 |

*Primary Examiner*—Michael Buiz
*Assistant Examiner*—Vy Q. Bui
*Attorney, Agent, or Firm*—Peter J. C. Esser

[57] ABSTRACT

A medical instrument driving member and end effector connection of the type having on the distal end of the instrument drive wire a hemispherical or knob-like terminus (38) which is seated so as to rotate freely in the countersunk bore (22) of the end effector tang (20), considerably reducing operating friction and permitting smooth and reliable opening and closing of the instrument end effectors (18), and rendering the entire device of a simpler construction and reliable in operation, while concurrently making it considerably less expensive to produce.

3 Claims, 1 Drawing Sheet

MEDICAL INSTRUMENT DRIVING MEMBER AND END EFFECTOR CONNECTION

BACKGROUND

1. Field of Invention

The present invention relates to endoscopic and related medical instruments, and more particularly, relates to a medical instrument incorporating a novel and unique arrangement for connecting an instrument end effector driving member such as a drive wire to the instrument end effector which will render the entire device of a simpler construction and reliable in operation, while concurrently making it considerably less expensive to produce.

BACKGROUND

2. Description of Prior Art

Although varied types of biopsy forceps are currently in widespread use, such as in conjunction with endoscopic purposes, these are generally of complicated constructions necessitating the manufacture and assembly of numerous, highly precise components and, as a consequence, are quite expensive. Ordinarily, an endoscopic biopsy forceps device must be sterilized in strict compliance with rigid medical standards after each use thereof with a patient, so as to enable the device to again be safely employed with another patient for subsequent medical and/or surgical endoscopic biopsy procedures. Such sterilizing procedures entail immersing and rinsing the contaminated endoscopic biopsy forceps devices in a suitable chemical sterilizing solutions and/or subjecting the biopsy devices to sterilizing in an autoclave. The sterilizing of the biopsy devices with the utilization of chemical sterilizing solutions has, in more recent years, given rise to concerns that the contaminated biopsy devices were not adequately sterilized for reuse with other patients, particularly in view of the considerable dangers to patients through exposure to potentially serious and even life-threatening infection with the AIDS virus (Acquired Immunity Deficiency Syndrome) or hepatitis B viruses, wherein sterilizing of the devices by means of such chemical solutions may not always be adequate to destroy the viruses, or at the very least, raise doubts as to the efficacy of the solutions. Furthermore, subjecting currently utilized endoscopic biopsy forceps devices to sterilizing procedures in an autoclave, under extremely rigorous physical conditions, frequently causes the rather delicate biopsy forceps devices to be destroyed, or damaged and warped to such an extent as to render the devices unusable for repeated applications.

In order to overcome the limitations and drawbacks which are currently encountered in the technology, and particular in endoscopy, with respect to the constructions and employment of endoscopic biopsy forceps which will meet with the requirements of the medical profession, the present invention contemplates the provision of an endoscopic biopsy forceps device which, to an appreciable and highly desirably extent, reduces the large number of components in each such device; and in particular, affords for a considerable reduction in the necessary articulated elements, pivot points, camming arrangements, rivets and attendant riveting operations in assembling the forceps device. In view of the complex construction of such prior art biopsy forceps devices are extremely expensive, and because it may not always be possible to properly sterilize the device to provide adequate safeguards against infections for patients exposed to previously used devices, rendering discarding thereof uneconomical, and possibly subjecting the medical facility and/or staff to legal liabilities in the event a patient is infected by a contaminated device. Moreover, the complex construction, method of attachment of driving elements to end effectors, and imprecise tolerances of the components often lead to rough operation of the device and damage to the sensitive linings of endoscopes. Rough operation of an instrument could possibly require a surgeon to perform a procedure several times in order to obtain the desired effect. Damage to an endoscope caused by protruding parts of an instrument would be undesirable due to the high cost of maintaining and replacing such equipment.

In the following discussion, "proximal" means that end of an instrument which is closest to the surgeon and farthest from the site of the operation, and "distal" means that end of the instrument which is farthest from the surgeon and closest to the site of the operation.

Among the typical types of endoscopic biopsy forceps and similar types of devices which are currently known, the following are fairly typical of the state of the technology. Bales et al. U.S. Pat. No. 5,133,727 (July, 1992) discloses a radial jaw biopsy forceps featuring a proximal handle attached to a driving member. Connected to the distal end of the driving member is a pair of jaws, each jaw having at its proximal end or tang a bore, through which a drive wire runs. The drive wire has at its distal end a Z-bend which secures it in place. This method of attachment creates friction when the end effectors or jaws are opened and closed, causing the device to operate less fluidly or smoothly than is desirable. The protruding parts commonly resulting from this configuration may also cause damage to the delicate lining of the working channel of the endoscope.

Bales et al. U.S. Pat. No. 5,666,965 (September, 1997) discloses a similar radial jaw biopsy forceps with a substantially similar method of attachment of the drive wire to the end effector as in the above referenced invention.

Oftentimes the prior art end effectors are formed by casting. Such a manufacturing process does not permit for precision tolerances, nor does it permit great latitude in designing strong and durable jaws with similarly precise and strong drive wire connection points. Specifically, a cast end effector must have simple recesses and through bores in order to preserve its structural integrity. The limitations of a simple through bore are numerous; for example, a drive wire may not be seated precisely, but rather usually runs through a bore and is loosely attached by angling or crimping the end alongside the end effector. The resultant jagged or protruding wire could possibly scratch the sensitive lining of an endoscope.

The prior art has attempted to overcome the limitations of cast end effectors by refining designs and in some cases totally abandoning the casting process in favor of machining. Other configurations have been proposed for connecting instrument driving members to instrument end effectors. Connections may for example take the form of staple like pins or welded contact points. The drawback to all of the existing connections is a tendency of the parts to wear, and for parts to protrude when the end effectors are in an open position. This hinders smooth, fluid operation of the mechanism and may result in endoscope damage. Moreover, such connections are disadvantageous in that they require labor-intensive assembly.

OBJECTS AND ADVANTAGES

Accordingly, it is an object of the present invention to provide a novel medical instrument driving element and end effector connection which overcomes the disadvantages of the prior art.

It is a further object of the present invention to provide a novel medical instrument driving element and end effector connection which will be smooth and positive in its operation.

It is another object of the present invention to provide a novel medical instrument driving element and end effector connection which will be secure and reliable.

It is yet another object of the present invention to provide a novel medical instrument driving element and end effector connection which is simple to manufacture, reliable, and low in cost, making one-way use an economical option.

It is still another object of the present invention to provide a novel medical instrument driving element and end effector connection which is harmless to the inner lining of an endoscope channel lining.

Still further objects and advantages will become apparent from a consideration of the ensuing description and accompanying drawings.

Figure 1:
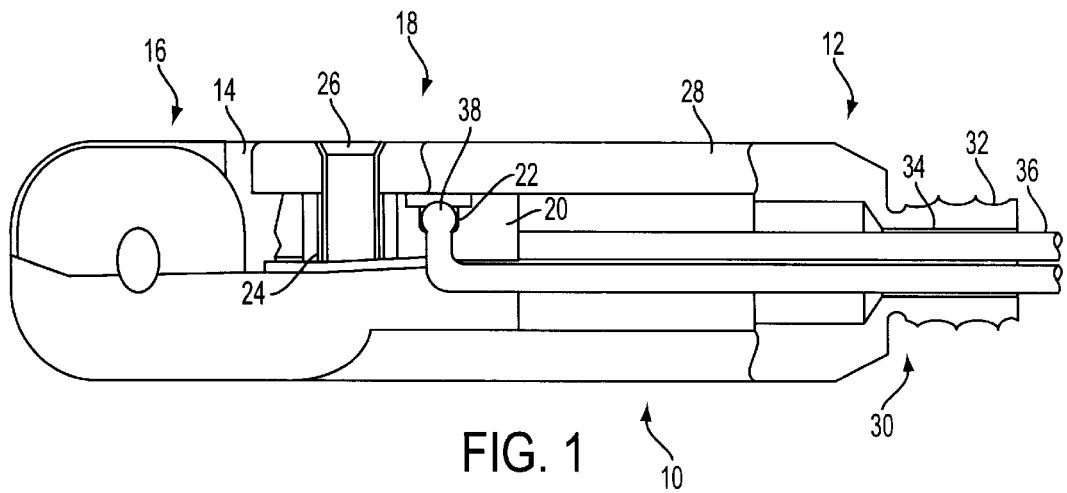
FIG. 1 is a plan view, partly in section, of the distal end of a biopsy forceps assembly.

| Reference Numerals in Drawings |
|---|
| 10 forceps assembly |
| 12 forceps assembly distal end |
| 14 jaw assembly |
| 16 forceps assembly proximal end |
| 18 jaw |
| 20 jaw tang |
| 22 jaw tang bore |
| 24 jaw bore |
| 26 rivet |
| 28 jaw housing |
| 30 jaw housing distal end |
| 32 jaw housing threaded base |
| 34 jaw housing distal end bore |
| 36 drive wire |
| 38 knob |

SUMMARY

In accordance with the present invention, an improved drive wire and end effector connection comprises a biopsy forceps jaw having at its proximal end a countersunk bore, into which the hemispherical distal terminus of a drive wire is inserted, permitting free and frictionless motion of the forceps jaw.

Figure 2:
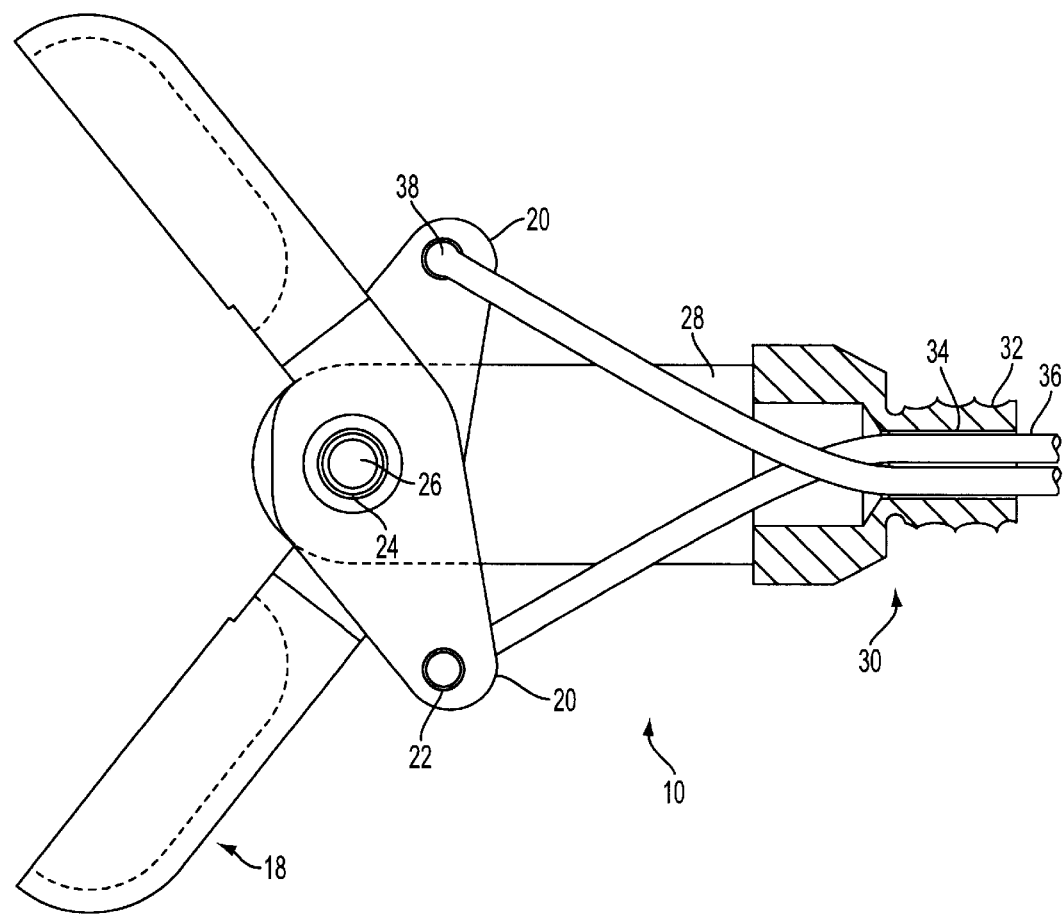
FIG. 2 is a side elevational, view partly in section, of the distal end of the biopsy forceps FIG. 1 with its jaws open.

Description—FIGS. 1 and 2

A typical embodiment of the drive wire and end effector connection of the present invention is illustrated in FIGS. 1 and 2. Referring now to the drawings in detail and particularly to FIG. 1, there is shown a biopsy forceps assembly 10, having a distal end 12, comprising a jaw assembly 14, and a proximal end 16 comprising a handle (not shown). The jaw assembly comprises a pair of mated jaws 18, each of which is a duplicate of the other. Each jaw 18 as may be seen in FIGS. 1 and 2 is a generally elongated structure having a distal end and a proximal end. Each jaw has a generally longitudinal centerline. The jaws 18 are in the preferred embodiment machined from stainless steel, providing a device with high tolerances.

Each jaw terminates proximally in a tang 20. Each tang has a bore 22 which, because the jaw is machined and therefore extremely strong, is countersunk on the outer side of the tang. A bore 24 extends transversely through approximately the midpoint of each jaw 18, and a rivet 26 running through the bore 24 permits secures the jaws 18 to the clevis-like forceps jaw housing 28, which is machined from stainless steel. The housing 28 has at its distal end 30 a threaded base 32 for connection to a drive wire sheath (not shown). A bore 34 extends through the distal end of the housing 28 and permits for passage of end effector drive wires 36.

The end effector drive wires 36 terminate distally in a spherical knob 38 which is slightly larger in diameter than the diameter of the drive wire.

Preferred Embodiment—Operation

The manner of using the drive wire and end effector connection follows. A drive wire 36 is drawn proximal end first through the outer side of the jaw tang bore 22, until the spherical distal knob seats in the countersunk outer side of the bore. The drive wire 36 is then manipulated so as to result in a 90-degree bend on the inner side of the jaw tang bore 22. The drive wire 36 is then inserted into the housing's distal bore 34. The drive wire may then be affixed to the proximal handle of the instrument (not shown).

Conclusions, Ramifications, and Scope

Accordingly, one skilled in the art will see that the drive wire and end effector connection of this invention will provide a means of attachment which is simple and reliable and low in friction. No jagged parts protrude upon opening the end effectors, thus protecting the interior of the endoscopes with which such instruments are commonly used. In addition, as the number of components is considerably reduced, the invention is simple to manufacture and low in cost.

Although the description above contains specificities, these should not be construed as limiting the scope of the invention but as merely providing illustrations of some of the presently preferred embodiments of this invention. For example, the drive wire's distal terminus could have other shapes compatible with a countersunk jaw tang bore and still capable of permitting free rotational movement.

Thus the scope of the invention should be determined by the appended claims and their legal equivalents, rather than by the examples given.

What is claimed is:

1. In a medical instrument driving member and effector connection assembly of the type comprising a flexible driving member distally connected to the proximal terminus of an end effector, the improvement wherein said flexible driving member is formed near its distal terminus into a 90-degree bend, and featuring at said distal terminus a spheroid or bulbous knob of slightly larger diameter than that of said flexible driving member as a whole, suitable for seating in a rounded countersunk or chamfered receptacle integral with said proximal end of said end effector.

2. The driving member and end effector connection of claim 1 wherein said driving member is composed of stainless steel wire and said distal terminus of said driving member is drawn or welded to a predetermined shape.

3. The driving member and end effector connection of claim 1 wherein said rounded receptacle of said end effector is a through bore which is countersunk or chamfered on its outer side for receiving said end effector terminus.

* * * * *